United States Patent [19]

Mitsumori et al.

[11] 4,045,553

[45] Aug. 30, 1977

[54] METHOD OF TREATING SILVER IMPREGNATED ACTIVATED CARBON

[75] Inventors: Nobuo Mitsumori; Chikahiro Takeda; Hideichi Miyasako, all of Kyoto, Japan

[73] Assignee: Nippon Shinyaku Company, Limited, Kyoto, Japan

[21] Appl. No.: 553,244

[22] Filed: Feb. 26, 1975

[51] Int. Cl.² .................... B01D 15/06; A61L 13/04
[52] U.S. Cl. .................... 424/132; 210/501; 210/32; 210/502; 55/59
[58] Field of Search .......... 55/59, 72; 210/501, 210/502, 504, 506, 509, 32, 40; 424/132

[56] References Cited

U.S. PATENT DOCUMENTS

| | | | |
|---|---|---|---|
| 1,557,235 | 10/1925 | Bechhold | 210/501 |
| 2,283,883 | 5/1942 | Conconi | 210/501 X |
| 3,193,987 | 7/1965 | Manes | 55/72 |
| 3,257,776 | 6/1966 | Park | 55/72 |
| 3,374,608 | 3/1968 | Manes | 55/72 |
| 3,596,438 | 8/1971 | Beukenkamp et al. | 55/59 |
| 3,638,399 | 2/1972 | Walker | 55/59 |

FOREIGN PATENT DOCUMENTS

| | | | |
|---|---|---|---|
| 2,364,504 | 8/1974 | Germany | 210/501 |

Primary Examiner—Frank A. Spear, Jr.
Assistant Examiner—E. Rollins Cross
Attorney, Agent, or Firm—Jacobs & Jacobs, P. C.

[57] ABSTRACT

The known sterilization and purification properties of activated carbon which is impregnated with silver are restored by treating spent silver impregnated activated carbon with steam.

1 Claim, 4 Drawing Figures

1. —●— Activated Carbon

2. —○— 0.1wt% Silver-Activated Carbon

Substance Adsorbed: 2-Hexenal

Adsorptive Power of Silver-Activated Carbon

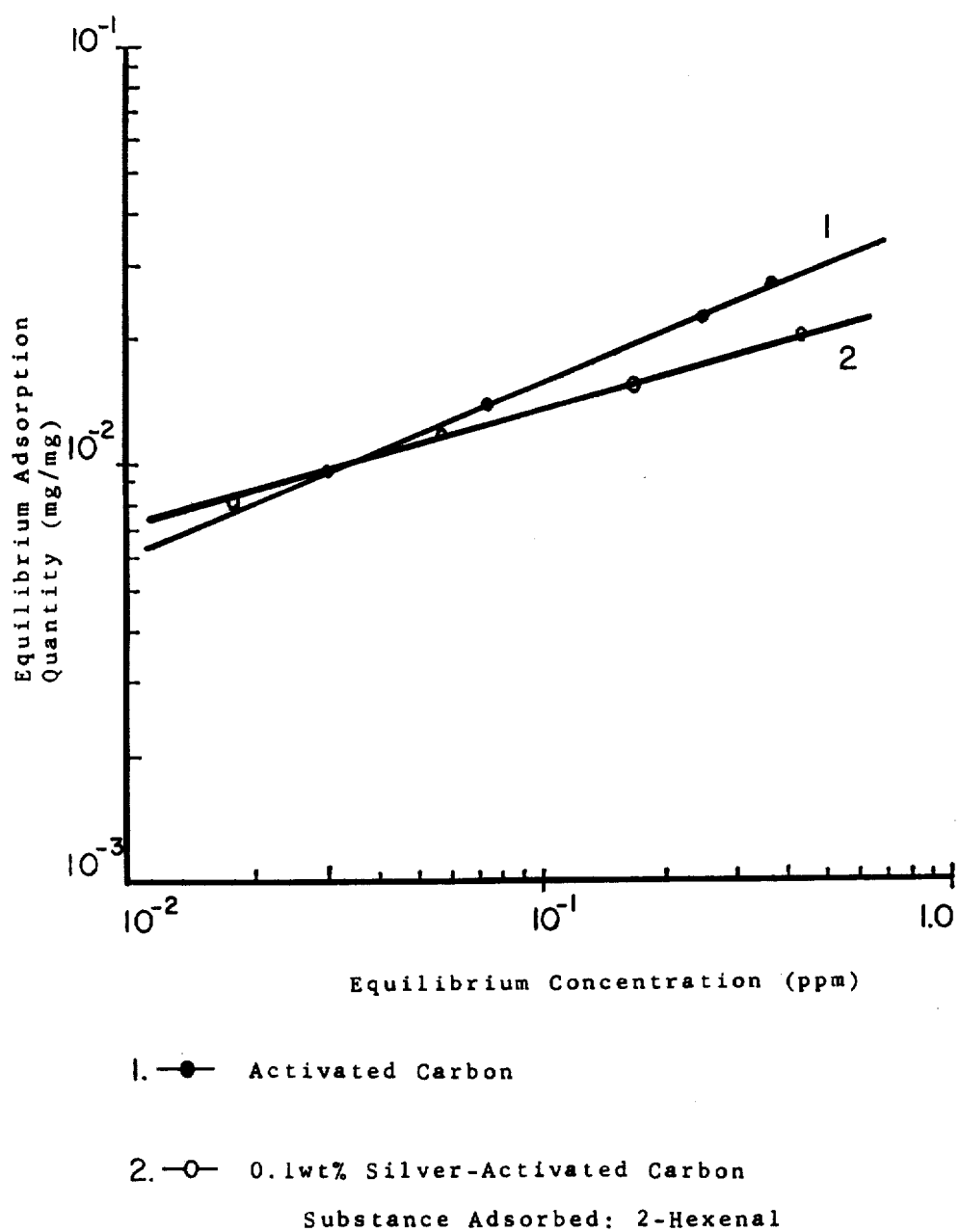
1. —●— Activated Carbon
2. —○— 0.1wt% Silver-Activated Carbon
Substance Adsorbed: 2-Hexenal
FIG. 1  Adsorptive Power of Silver-Activated Carbon

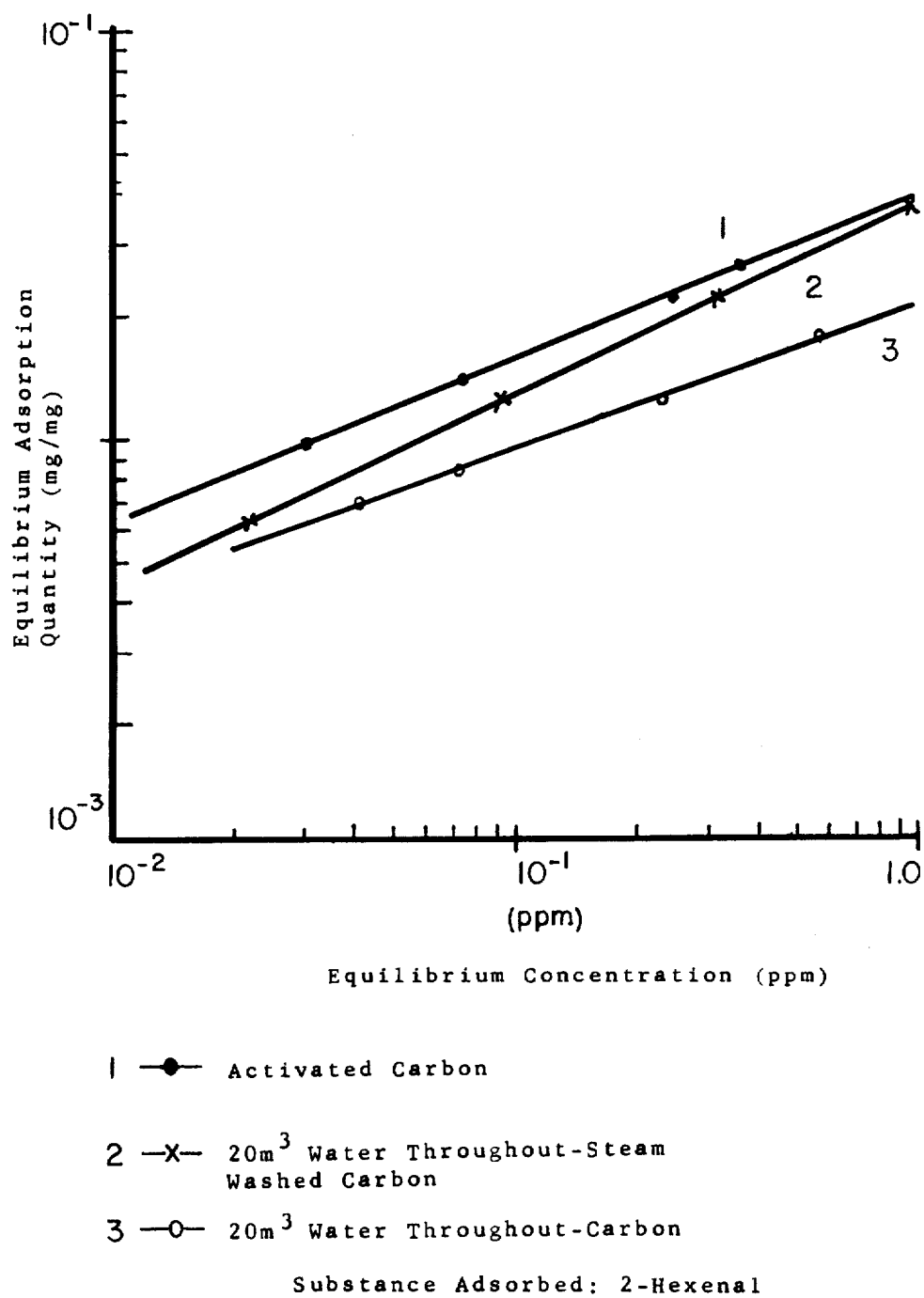
FIG. 2 Effect of Steam-Washing of Activated Carbon

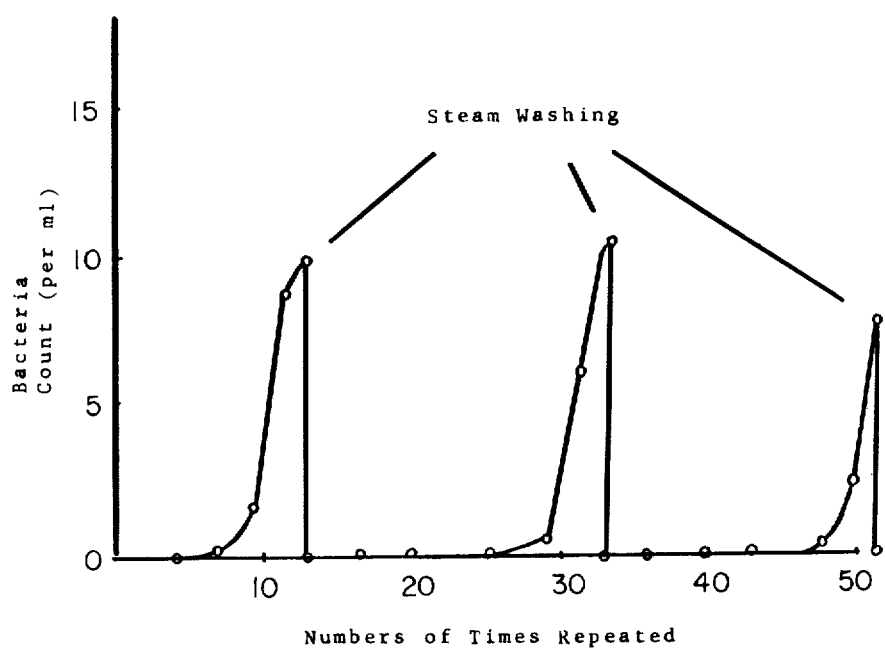
FIG. 3  Restoration and Duration of Sterilization Property of Silver-Activated Carbon
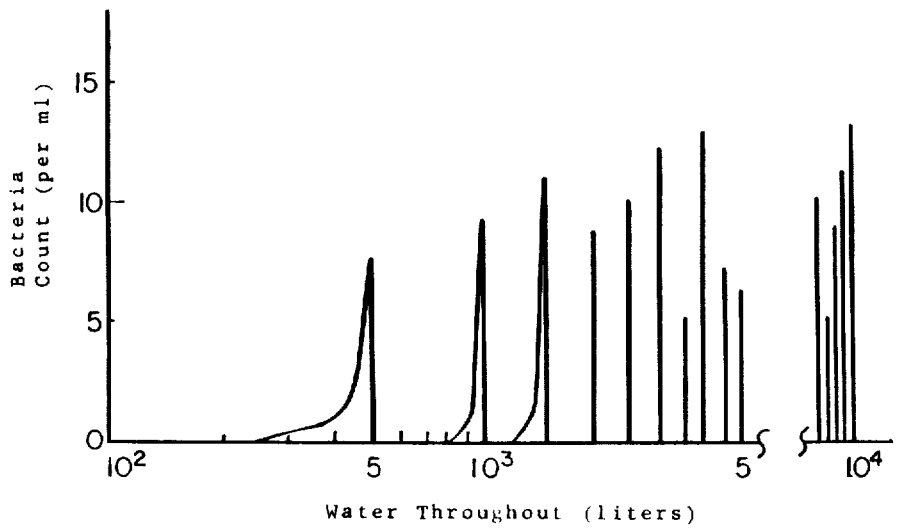
FIG. 4  Maintenance of Restoration Property of Sterilization Power when Used in a Water Purifier ically absorption analysis, is 0.005 ppm, which is much
METHOD OF TREATING SILVER IMPREGNATED ACTIVATED CARBON The use of activated carbon which has been impregnated on its surface with silver in various sterilization and purification procedures is well known. Thus for example U.S. Pat. No. 3,374,608 describes the use of such a catalyst in the removal of mercury vapor. The material is also used for the purification of water containing bacteria, the clarification of rice wine, and the prevention of various plant diseases. Methods of impregnating silver on the surface of activated carbon are also widely known, see e.g. U.S. Pat. No. 3,294,572.

It is also known however that in the course of such usage, organic substances accumulate on the surface of the material and this results in a large reduction in the material's capacity to effect sterilization. The inherent adsorptive powers of the activated carbon are also reduced in the course of use, although the rate of this reduction is somewhat lower than the reduction in the sterilization properties, see e.g. Vaprosy Pitaniya, Vol. 5, No. 6, 85-96, and Eisei Shikenjo Hokoku, Vol. 50, 58. Hence while silver impregnated activated carbon has the potential for widespread use in the sterilization and purification of liquids, the rapidity with which the material becomes spent is such that such widespread use has not yet been realized.

The present invention pertains to a method for restoring the sterilization and purification properties of silver impregnated activated carbon so as to prolong the sterilization effect and prevent undesired decreases in the adsorptive properties of the activated carbon. The nature of the invention will be apparent from the following description and from the appended drawings in which:

FIG. 1 is a plot showing the equilibrium adsorptive power of silver impregnated activated carbon;

FIG. 2 is a plot showing the effect of steam on activated carbon which has not been impregnated with silver;

FIG. 3 is a plot showing the duration of the sterilization properties of silver impregnated activated carbon and the cyclical restoration of these properties after use; and FIG. 4 is a plot showing maintenance and restoration of the sterilization properties in actual use in a water purifier.

Metallic silver is impregnated on activated carbon when activated carbon is added to an aqueous solution of a silver salt. For example, 0.1 wt. percent silver activated carbon, which is the composition most frequently used, is prepared by adding activated carbon to about 500 ppm silver nitrate solution. Solutions of the silver salts of organic acids, such as silver lactate and silver citrate, can also be used. Activated carbon loses its absorption property when a large quantity of silver is impregnated but there is almost no change in the adsorptive power when the quantity of impregnated silver is small, e.g., below 1.0 wt. percent, as indicated in the adsorption isotherm curve of FIG. 1. For example, activated carbon with 0.1 wt. percent of silver impregnated on it can sterilize and clear water containing several $10^3$ to $10^4$ ordinary bacteria per ml, as described in Experiment 2. Furthermore, the silver ion concentration in clear water obtained after passing service water through silver activated carbon when measured by atomic absorption analysis, is 0.005 ppm, which is much lower than the 0.05 ppm called for by the American Public Health Association's "Drinking Water Standards". Moreover, and as a general rule, chlorine is adsorbed when service water is passed through activated carbon so that the ordinary bacteria can then propagate. When water is passed through silver impregnated activated carbon, ordinary bacteria will not propagate because a micro quantity of silver is present, see e.g., Experiment 3. However, when such silver activated carbon is used continuously as in the sterilization and purification of water, the sterilization effect of silver activated carbon decreases, presumably due to organic substances and dead bacteria which were contained in the water collecting on the surface of the material.

The present invention is based on the discovery that the sterilization effect is restored and maintained for some time when steam is passed through the silver impregnated activated carbon whose sterilization effect has decreased; i.e. spent material. Additionally it was found that the characteristic sterilization effect of silver impregnated activated carbon does not materially decrease as a result of elution of silver. Presumably this is because the eluted quantity of silver by washing with steam is very small, e.g., about 0.001 ppm.

The effect of restoring the sterilization properties of silver impregnated activated carbon by washing with steam does not appear to be dependent upon the method of preparation of the silver impregnated activated carbon. Thus the same effect is observed whether the activated carbon is impregnated with silver directly without the use of a reducing agent, as by adding activated carbon to a solution of a silver salt such as silver nitrate or the silver salt of an organic acid, or whether the impregnation is effected by reducing silver nitrate with a reducing agent such as tannic acid, formalin or sodium thiocyanate.

Not only is the use of steam effective for restoring the sterilization properties of silver impregnated activated carbon prepared by different methods, the process also suppresses a reduction of the adsorptive power of the activated carbon itself, as shown in Experiment 4 described below.

It is known that, as a general rule, in case of water purifiers in which only activated carbon is used, bacteria, which either were present in the service water or entered from some other route, increase with time. So-called purified water may thus have counts of ordinary bacteria over 100 per ml which is undesirable from the sanitation point of view.

The present applicants previously invented an improved water sterilizer-purifier in which complete sterilization is carried out in the purifier by passing steam into the water purifier but this arrangement was inconvenient since the steam sterilization operation must be carried out at least once a day. However, as a result of the present invention, that is, the steam restoration operation, and the use of silver impregnated activated carbon in place of simply activated carbon as the adsorption agent, the sterilization effect of silver-activated carbon is prolonged for a minimum of 10 days without any lowering of the adsorptive power of the activated carbon.

Thus, recovery of the sterilization effect and also suppression of lowering of the adsorptive power were obtained in the present invention by carrying out steam washing of the silver impregnated activated carbon. As a result, silver impregnated activated carbon which has been spent or poisoned can be recovered and repeatedly used.

The following four experiments pertain to the materials employed and the parameters of their properties. The bacteria test was carried out in accordance with the bacteria testing method of the service water testing method of the Japan Water Supply Association.

Experiment 1

Equilibrium adsorptions of the conventional activated carbon and 0.1 wt. percent silver activated carbon were obtained using 2-hexenal. The results are shown in FIG. 1. It is clear from the figure that there is almost no difference in the adsorptive power of silver impregnated on activated carbon and activated carbon itself.

Experiment 2

Service water from which residual chlorine has been removed and the ordinary bacteria allowed to propagate to bacteria count is 30,000 per ml was fed to a column 24 mm in diameter and 60 mm in height packed with 20 g of 0.1 percent silver impregnated activated carbon which has been washed with steam beforehand at a linear velocity of 80 cm/min. No bacteria was found in the effluent.

Experiment 3

Service water containing ordinary bacteria was added to the effluent of Experiment 2 and the bacteria count adjusted to 5,000 per ml, cultured for 3 hours at 30° C. When tested, it was found that the bacteria count was 0.

Experiment 4

The effect on the adsorptive powers of activated carbon which is washed with steam was investigated by passing service water through activated carbon to adsorb the impurities in the service water. Total water throughout was 20 m$^3$ and steam washing was carried out every 50 liters to 100 liters. The difference in the adsorptive capacity using 2-hexenal was obtained by measuring the adsorption isotherm of carbon through which water has not been passed, carbon through which water has been passed and steam-washed carbon. The results are shown in FIG. 2. It can be seen from this that the reduction in the adsorptive power of activated carbon is suppressed by carrying out steam washing.

The following examples will serve to further typify the nature of this invention without being a limitation on the scope thereof, the scope being defined solely by the appended claims.

EXAMPLE 1

5 g of 0.1 wt. percent silver activated carbon which has been treated beforehand by steam washing was placed in a 50 ml Erlenmeyer flask, 25 ml of water containing 2,000–10,000 per ml of ordinary bacteria was added to this, left standing for 3 hours at 30° C and the bacteria count of the water was then measured. This was next filtered in a sterile room, the silver impregnated activated carbon which was collected was dried, heat-sterilized for 45 min. at 180° C and dried, and water containing ordinary bacteria (2,000 – 10,000 per ml) was added. The above procedure was repeated without steam washing. It was found that the ordinary bacteria started to increase in number after about the 10th cycle, indicating a loss in activity. Silver activated carbon which has lost activity in this manner was then washed by passing steam through it. The sterilization effect was thus restored and there was no increase in bacteria even after passing water through the 20th time (see FIG. 3).

EXAMPLE 2

500 g of 0.1 wt. percent silver-activated carbon was packed in a sterilization purified cartridge 9 cm inside diameter, 15 cm height and steam-washing was carried out. Service water was passed through the cartridge at a rate of 50 liters/day. The silver activated carbon was treated with steam once every 500 liters of water fed. The silver content in the water was investigated for 50, 500, 1,500, 3,000, 6,000 and 10,000 liters throughputs. It was found that the silver content after a throughput of 10000 liters of water was 0.001–0.01 ppm, which was about the same as that of the initial period of water feed. Also, water containing about 5,000 per ml of ordinary bacteria was passed for each throughput of 500 liters and the bacteria count at the outlet was measured to investigate the duration for which the sterilization power was maintained. Steam washing was then carried out, the material was cooled, water containing about 5,000 per ml of ordinary bacteria was fed through it and the bacteria count of the output was measured. The bacteria count before steam washing was about 10 but this became 0 after steam washing and the condition remained the same even after a water throughput of 10,000 liters. It was found that the material can be used for a long time as a result of the recovery of its sterilization power by steam washing (see FIG. 4). The equilibrium adsorptive quantity of 2-hexenal after a water throughput of 10,000 liters was also measured for silver impregnated activated carbon and it was found that the difference in its adsorption capacity was small as compared with silver impregnated activated carbon through which water has not been passed.

What is claimed is:

1. The method of restoring the sterilization and purification properties of silver impregnated activated carbon which comprises subjecting spent silver impregnated activated carbon to the action of steam until said properties are restored.

* * * * *